United States Patent [19]

Biblarz

[11] 4,304,124

[45] Dec. 8, 1981

[54] CHARGING MECHANISMS FOR ELECTROGASDYNAMIC SPECTRAL ANEMOMETER

[75] Inventor: Oscar Biblarz, Carmel, Calif.

[73] Assignee: The United States of America as represented by the Secretary of the Navy, Washington, D.C.

[21] Appl. No.: 93,790

[22] Filed: Nov. 13, 1979

[51] Int. Cl.$^3$ .................. G01P 13/00; G01W 1/02; G01N 27/64

[52] U.S. Cl. .................. 73/861.09; 73/147; 73/189

[58] Field of Search .............. 73/861.09, 147, 189; 324/459, 464, 465; 250/382

[56] References Cited

U.S. PATENT DOCUMENTS

| | | | |
|---|---|---|---|
| 2,637,208 | 5/1953 | Mellen | 73/861.05 |
| 2,640,936 | 6/1953 | Pajes | 73/861.05 |
| 2,820,945 | 1/1958 | Marsden, Jr. | 324/464 |
| 2,861,452 | 11/1958 | Morgan | 73/861.09 |
| 3,478,204 | 11/1969 | Brubaker et al. | |
| 3,718,043 | 2/1973 | Fishman et al. | 73/861.05 |
| 3,777,564 | 12/1973 | Biblarz | 73/861.09 |
| 4,090,856 | 5/1978 | Rogoff | 250/423 P X |

Primary Examiner—James J. Gill
Attorney, Agent, or Firm—R. S. Sciascia; Charles D. B. Curry; Francis I. Gray

[57] ABSTRACT

A practical charging mechanism for an electrogasdynamic spectral anemometer using ultraviolet radiation. Ultraviolet radiation issues through windows in the wall of a test section through which flows a turbulent gas. The UV ionizes aerosol particles in the gas flow. A metallic rod which is connected to a high voltage source picks up ions of one polarity and a collector downstream neutralizes the ions of the opposite polarity. The current generated at the collector is measured and analyzed.

11 Claims, 1 Drawing Figure

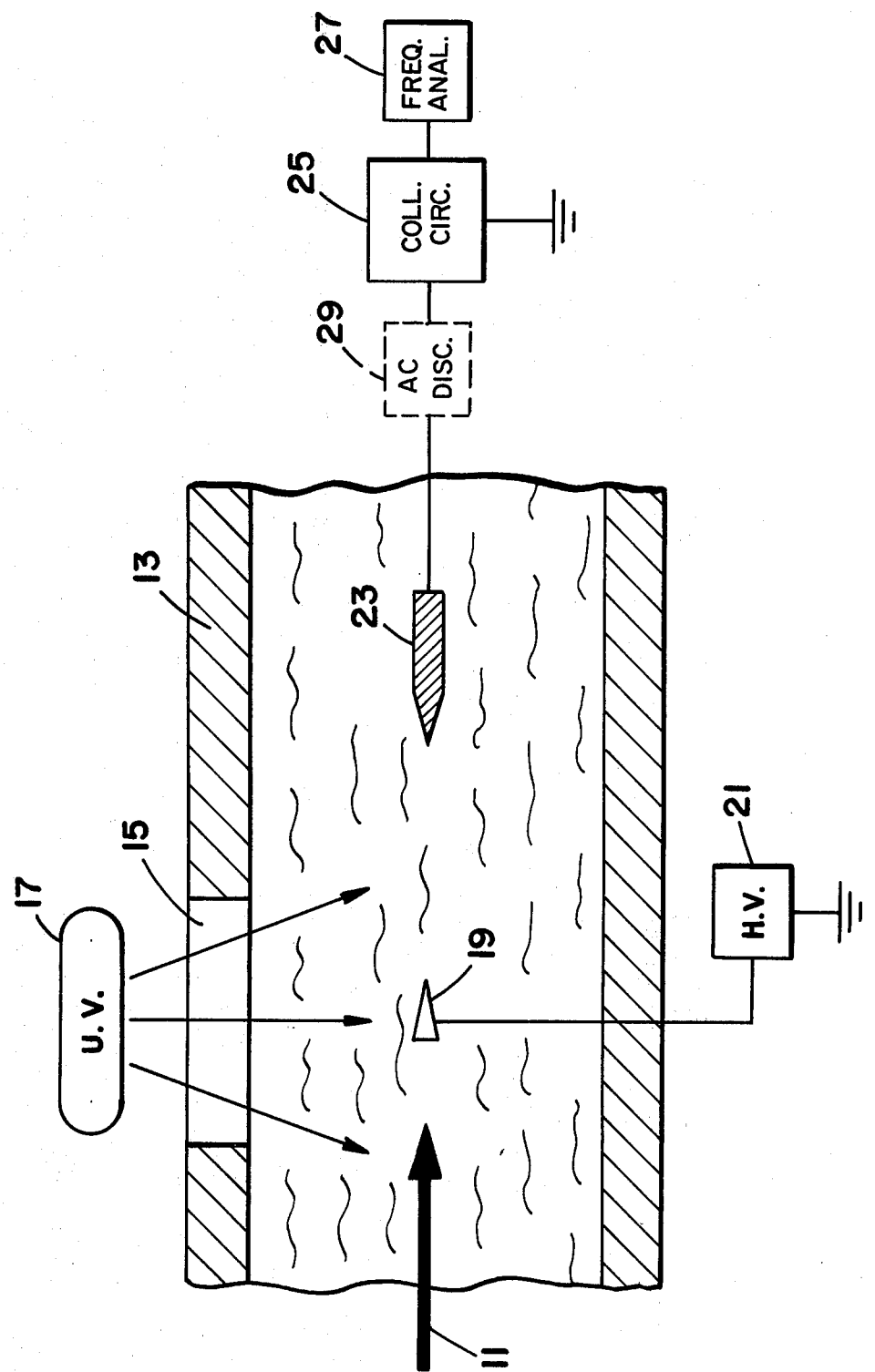

CHARGING MECHANISMS FOR ELECTROGASDYNAMIC SPECTRAL ANEMOMETER

BACKGROUND OF THE INVENTION

1. Field of the Invention

The present invention relates to electrogasdynamic spectral anemometers, and more particularly to alternate charging mechanisms.

2. Description of Prior Art

The charging mechanism for an electrogasdynamic spectral anemometer described in U.S. Pat. No. 3,777,564, issued Dec. 11, 1973 to Oscar Biblarz, and in the Journal of Electrostatics, Vol. 5 (1978) pgs 101-120, both entitled "electrogasdynamic Spectral Anemometer", consists of passing a condensable vapor through a corona discharge. This mechanism is dependent upon the existence of a supersaturated vapor in the discharge region which causes some inconvenience. Also, the blockage by the injector unit produces sizable penalties in pressure drop and affects the turbulence spectrum to be measured.

SUMMARY OF THE INVENTION

Accordingly, the present invention provides a more practical charging mechanism using ultraviolet (UV) radiation. UV-radiation issues through windows in the walls of a test section through which flows the turbulent stream under investigation and is focused in different regions of the stream. A collector, inserted in the stream, is traversable together with a slender, metallic rod. The rod is connected to a high voltage source and separates the positive and negative ions generated by the ultraviolet radiation. A collector downstream neutralizes the ions not picked up by the rod and produces a current which is measured and analyzed.

Alternatively the UV-radiation is focused on a photoelectric emitter at the tip of a highly negatively charged rod. The emitted electrons attach to the particles of the stream and are convected by the flow to the collector.

Therefore, it is an object of the present invention to provide a more practical charging mechanism for an electrogasdynamic spectral anemometer.

Another object of the present invention is to minimize the blockage caused by the injector.

Still another object of the present invention is to eliminate the use of supersaturated steam as part of the charging mechanism.

Other objects, advantages and novel features of the present invention will be apparent from the following description when read in view of the appended claims and attached drawing.

BRIEF DESCRIPTION OF THE DRAWING

The FIGURE is a schematic diagram of an electrogasdynamic spectral anemometer according to the present invention.

DESCRIPTION OF THE PREFERRED EMBODIMENT

Referring now to the FIGURE a turbulent gas flow 11 is introduced to a test section 13. An ultraviolet window 15 in the wall of the test section 13 allows a source of ultraviolet radiation 17 to ionize the gas flow 11. A rod 19 is charged by a high voltage source 21 to pick up either positive or negative ions, depending upon the composition of the gas flow 11, from the ionized gas flow. A collector 23 downstream from the rod 19 neutralizes the remaining ions and transmits a signal to a collector circuitry 25. The output of the collector circuitry 25 is input to a frequency analyzer 27 which provides information about the intensity of the turbulence at the various frequencies of interest.

Ultraviolet radiation spans the spectrum of from about 3 to 100 electron volts, which is ample energy to ionize the atoms and molecules in any glass flow. (X-rays would be equally good, but are more difficult to obtain and to handle.) Moreover, aerosols are even easier to ionize than their parent atoms, and atmospheric flows typically contain aerosols in the optimal size of about $10^{-7}$ m which are entrained in the flow. Aerosols also may be readily introduced, i.e., seeded as in the laser doppler anemometer. So, whether the aerosol is ionized directly or is charged with electrons produced from the background gas ionization, ultraviolet radiation, such as from a lamp or a discharge, is a practical source of ionization.

In operation the ultraviolet radiation from the source 17 issues from the walls of the test section 13 through the window 15 and is focused in different regions of the gas flow 11. The high voltage supply 21 may be either a dc source of either polarity (depending upon the composition of the gas flow 11) or an ac source. For an ac source an ac discriminator 29 is inserted between the collector 23 and the collector circuitry 25 to remove the basic ac component before analysis by the frequency analyzer 27. The rod 19 picks up the ions of one polarity and may be traversed in conjunction with the collector 23 to sample the entire gas flow 11. The remaining ions are then neutralized by the collector 23 and the resulting current analyzed as previously described.

Alternatively for very clean gas flows the rod 19 could have a suitable photoelectric emitter at the tip and be highly negatively charged. When the ultraviolet radiation is focused on the tip, electrons are emitted which attach to the aerosol particles and are convected by the flow to the collector 23. This mechanism requires less ultraviolet energy since the aerosol is not ionized by the ultraviolet radiation.

The separation between the rod 19 and the collector 23 is a function of the desired sensitivity. If the rod and collector are too close, then what is being analyzed is the turbulence caused by the rod rather than that of the gas flow, or else a corona discharge could occur. If the distance is too great, then the sensitivity is reduced, sensitivity being a function of the distance as well as the collector circuitry 25. A distance up to 1 cm has been found to be optimum.

Using high voltage ac for the voltage source 21 reduces the possibility of the back corona as well as providing the freedom to select either type of ion by adjusting the ac discriminator 29.

Thus the present invention provides an alternate charging mechanism for an electrogasdynamic spectral anemometer which minimizes the blockage of an injector, eliminates the requirement for a supersaturated vapor, and results in a factor of 2 or more improvement in the practicality of the electrogasdynamic spectral anemometer.

What is claimed is:

1. An apparatus for measuring the dynamic characteristics of a gas flow comprising:

(a) means for charging particles in said gas flow, said means for charging including a source of ultraviolet radiation directed into said gas flow;

(b) means situated downstream from said charging means for neutralizing said charged particles from said gas flow; and (c) means for measuring the charge and frequency of said charged particles neutralized by said neutralizing means.

2. An apparatus as recited in claim 1 wherein said charging means comprises:

(a) a source of ultraviolet radiation focused on said gas flow, said ultraviolet radiation having sufficient energy to ionize aerosols contained in said gas flow to generate said charged particles; and (b) means for separating the ions of opposite polarity which make up said charged particles.

3. An apparatus as recited in claim 2 wherein said separating means comprises:

(a) a slender, metallic rod situated in said gas flow; and (b) a high voltage source connected to said rod to induce a charge which neutralizes charged particles of opposite polarity to the charged particles neutralized by said neutralizing means.

4. An apparatus as recited in claim 3 wherein said high voltage source comprises a high voltage ac source.

5. An apparatus as recited in claim 4 further comprising an ac discriminator connected between said neutralizing means and said measuring means to compensate for the ac signal introduced by said high voltage ac source and to select the polarity of said charged particles to be processed by said measuring means.

6. An apparatus as recited in claim 1 wherein said charging means comprises:

(a) a highly charged slender metallic rod having a tip of a photoelectric emitter material; and (b) a source of ultraviolet energy focused on said tip to cause electrons to be emitted, said electrons attaching to aerosol particles of said gas flow to form said charged particles.

7. Apparatus for measuring the dynamic characteristics of a gas flow comprising:

(a) a source of ultraviolet radiation focused on said gas flow, said ultraviolet radiation having sufficient energy to ionize aerosols contained in said gas flow to generate charged particles;

(b) first means for neutralizing charged particles of a selected polarity, said first neutralizing means being disposed downstream from said source of ultraviolet radiation;

(c) second means for neutralizing charged particles of a selected polarity, said second neutralizing means being disposed downstream from said first neutralizing means; and (d) means for measuring the charge and frequency of the charged particles neutralized by said second neutralizing means.

8. Apparatus as recited in claim 7 wherein said first neutralizing means comprises:

(a) a slender, metallic rod situated in said gas flow; and (b) a high voltage source connected to said rod to induce a charge which neutralizes charged particles of opposite polarity to the charged particles neutralized by said second neutralizing means.

9. Apparatus as recited in claim 8 wherein said high voltage source comprises a high voltage ac source.

10. Apparatus as recited in claim 9 further comprising an AC discriminator connected between said second neutralizing means and said measuring means to compensate for the ac signal introduced by said high voltage ac source and to select the polarity of said charged particles to be processed by said measuring means.

11. Apparatus for measuring the dynamic characteristics of a gas flow comprising:

(a) a highly charged slender metallic rod having a tip of a photoelectric emitter material;

(b) a source of ultraviolet energy focused on said tip to cause electrons to be emitted, said electrons attaching to aerosol particles to said gas flow to form charged particles;

(c) means for neutralizing said charged particles, said neutralizing means being disposed downstream from said metallic rod; and (d) means for measuring the charge and frequency of the charged particles neutralized by said neutralizing means.

* * * * *